United States Patent [19]

Musser et al.

[11] Patent Number: 4,530,931

[45] Date of Patent: Jul. 23, 1985

[54] 8-QUINOLINE CARBANILATES FOR THE INHIBITION OF LIPOLYSIS

[75] Inventors: John H. Musser, Malvern, Pa.; Charles A. Sutherland, Hawthorne, N.Y.

[73] Assignee: USV Pharmaceutical Corp., Tarrytown, N.Y.

[21] Appl. No.: 591,702

[22] Filed: Mar. 21, 1984

Related U.S. Application Data

[63] Continuation of Ser. No. 455,377, Jan. 3, 1983, abandoned.

[51] Int. Cl.³ .................. A61K 31/47; C07D 215/16; C07D 215/20; C07D 215/38
[52] U.S. Cl. .................. 514/312; 514/313; 546/153; 546/155; 546/157; 546/159; 546/171; 546/174; 546/175; 546/178; 546/183
[58] Field of Search ........... 546/171, 174, 153, 175, 546/155, 178, 157, 159, 183; 424/258

[56] References Cited

U.S. PATENT DOCUMENTS 3,538,099 11/1970 Rohr et al. ............... 546/175
3,946,016 3/1976 Karsten et al. .............. 424/258

FOREIGN PATENT DOCUMENTS 989578 4/1965 United Kingdom ............ 546/174

OTHER PUBLICATIONS

Somasekhara, Chem. Abst., vol. 70 (1969), 11532w.
Somasekhara, Current Science 37(19): 551-2, 1968.

Primary Examiner—Donald G. Daus
Assistant Examiner—Cecilia Shen

[57] ABSTRACT

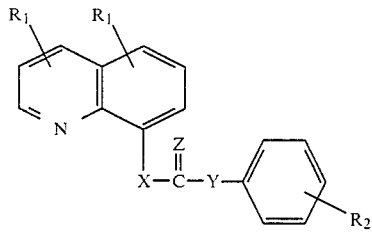

and pharmaceutically acceptable salts thereof wherein:
$R_1$ is H, alkyl, alkoxy, trihalomethyl, and chlorine;
X is in the 8 position and is $O(CH_2)_n$, $N(CH_2)_n$;
Y is $O(CH_2)_n$, $N(CH_2)_n$;
$R_2$ is monosubstituted or independently disubstituted H, carboxyl, or alkylcarboxy;
Z is O; and
n is 0 to 10 inclusive, useful in the treatment of ischemic heart disease and hypertriglyceridemia.

3 Claims, No Drawings

8-QUINOLINE CARBANILATES FOR THE INHIBITION OF LIPOLYSIS

RELATED APPLICATIONS

This application is a continuation of our copending application, Ser. No. 455,377, filed Jan. 3, 1983, now abandoned.

DESCRIPTION OF THE PRIOR ART

We have found that quinoline carbanilates are active antilipolytic agents as evidenced by the myocardial lipase and the rat adipocyte assays.

Lipolysis is associated with ischemic heart disease: free fatty acid has a detrimental effect on the ischemic heart by disrupting electrical conduction, decreasing myocardial efficiency and preventing the transfer of adenosine diphosphate and adenosine triphosphate, in and out, respectively, of the mitochondria. Interventions which depress myocardial oxygen consumption in animals and man provide a protective effect against ischemic injury.

The object of this invention is to provide compounds capable of inhibiting lipolysis associated with ischemic heart disease.

We have found that 8-quinoline carbanilates are active antilypolytic agents. 8-quinoline carbanilates are known as fungacides, pesticides, amebicides and bactericides.

DESCRIPTION OF THE INVENTION

This invention relates to chemical compounds possessing valuable pharmaceutical activity useful in the treatment of ischemic heart disease and hypertriglyceridemia and having the structure:

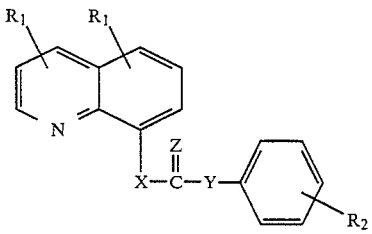

and pharmaceutical acceptable salts thereof wherein:
- $R_1$ is H, alkyl, alkoxy, carboxyl, alkylcarboxy, acylamino, dialkylamino, trihalomethyl, halogen, nitro, hydroxy or cyano;
- X is in the 8 position and is $O(CH_2)_n$, $N(CH_2)_n$, $S(CH_2)_n$ or $(CH_2)_n$;
- Y is $O(CH_2)_n$, $S(CH_2)_n$, $N(CH_2)_n$;
- $R_2$ is monosubstituted or independently disubstituted H, hydroxy, alkyl, halogen, nitro, alkoxy, carboxyl, alkylcarboxy, cyano, trihalomethyl, dialkylamino or acylamino;
- Z is O; and
- n is 0 to 10 inclusive useful in the treatment of ischemic heart disease and hypertriglyceridemia.

The alkyl group and the alkyl moieties in alkoxy and alkylcarboxy contain 1 to 7 carbon atoms and may be a straight or a branched chain. Such groups include methyl, ethyl, propyl, isopropyl, butyl, isobutyl, amyl, isoamyl and the like.

The trihalo and halogen are F, Cl, Br or I.

The aryl group is preferably phenyl or naphthyl.

The compounds of this invention may be readily prepared by reacting the appropriate quinolinol with various substituted phenyl isocyanates. The reaction is thermally reversible and for that reason the preferred procedure involves the mixing of the two reactants in ethyl ether with a small amount of triethylamine present as a catalyst and stirring at room temperature for several days.

The schematic procedure is as follows:

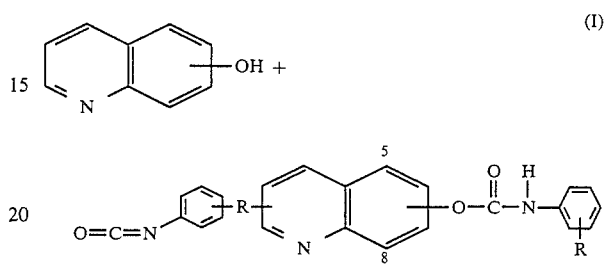

Alternatively, the phenylesters of 8-quinoline carbamic acid may also be prepared by treating 8-aminoquinoline with phosgene to obtain intermediate II. Reaction of II with different phenols in THF at room temperature with an equivalent of triethylamine produces substituted phenyl 8-quinoline carbamates III.

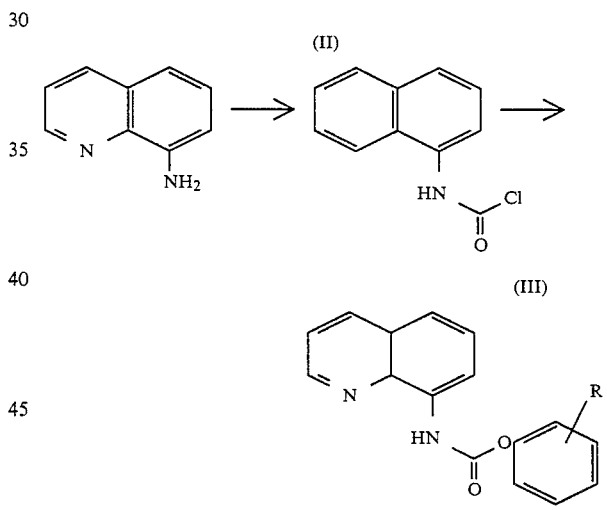

The desired starting materials and intermediates can be prepared from readily available materials using standard organic reactions. Some starting materials and intermediates are also available from chemical supply companies, such as Aldrich and Pfaltz & Bauer.

The invention will be more fully illustrated in the examples that follow. These examples are given by way of illustration and are not to be considered as limiting.

EXAMPLE 1

8-Quinolyl-4-Methoxy Carbanilate

To a solution of 8-hydroxyquinoline (1.45 g., Aldrich 16498-4) and 4-methoxyphenyl isocyanate (1.49 g.) in ethyl ether (100 ml) was added triethylamine (1.4 ml). The reaction was stirred for two days at room temperature. The resulting precipitate was filtered and recrystallized from ethyl ether (1.9 g., 65% yield); m.p. 129°–130°

In like manner as above, using appropriate starting materials and reagents, the following compounds were prepared:

EXAMPLE 2
8-quinolyl-2-methoxy carbanilate

EXAMPLE 3
8-quinolyl-3-methoxy carbanilate

EXAMPLE 4
8-quninolyl-4-carbethoxy carbanilate

EXAMPLE 5
8-quinolyl-4-chloro carbanilate

EXAMPLE 6
8-quinolyl-3-chloro carbanilate

EXAMPLE 7
8-quinolyl-2-chloro carbanilate

EXAMPLE 8
8-quinolyl-4-methyl carbanilate

EXAMPLE 9
8-quinolyl-3-methyl carbanilate

EXAMPLE 10
8-quinolyl-2-methyl carbanilate

EXAMPLE 11
8-quinolyl-3-trifluoromethyl carbanilate

EXAMPLE 12
8-quinolyl-2,4-dimethoxy carbanilate

EXAMPLE 13
8-quinolyl-2,5-dimethoxy carbanilate

EXAMPLE 14
8-quinolyl-4-bromo carbanilate

EXAMPLE 15
8-quinolyl-carbanilate

EXAMPLE 16
2-methyl-8-quinolyl carbanilate

EXAMPLE 17
2-methyl-8-quinolyl-4-methoxy carbanilate

EXAMPLE 18
2-methyl-8-quinolyl-4-bromo carbanilate

EXAMPLE 19
5-chloro-8-quinolyl carbanilate

EXAMPLE 20
5,7-dichloro-8-quinolyl carbanilate

EXAMPLE 21
8-quinolyl-4-methoxy benzyl carbamate

EXAMPLE 22
8-quinolyl-4-methoxy phenethyl carbamate

EXAMPLE 23
(S)8-quinolyl alpha-methyl benzyl carbamate

EXAMPLE 24
(R)8-quinolyl alpha-methyl benzyl carbamate

EXAMPLE 25A
8-Quinolylcarbamyl Chloride

8-Aminoquinoline (2.0 g., Pfaltz & Bauer, A28560) in methylene chloride (10 ml) was added dropwise to a 0° C. solution of 2.2M phosgene in methylene chloride (12 ml). The resulting precipitate was filtered and dried. The dark solid thus obtained is unstable and in practice it was immediately used in the next reaction.

EXAMPLE 25B
4-Methoxyphenyl-8-quinolyl carbamate

A suspension of 8-quinolylcarbamyl chloride (5.7 g.) in dry THF (100 ml) was treated with triethylamine (20 ml). 4-Methoxyphenol (3.4 g.) was then added and the reaction was allowed to stir overnight at room temperature. The solvent was removed in vacuo. The residue was dissolved in chloroform and washed with 1N sodium hydroxide (two times), water; dried (MgSO$_4$) and concentrated to a solid. The solid was dissolved in a 1:1 mixture of ethyl acetate and acetone, treated with charcoal and filtered through a pad of celite and silica gel. A crystalline solid formed which was filtered and dried (315 g., 43% yield); m.p. 128°–129° C.

In like manner as above, using appropriate starting materials and reagents, the following compound was prepared:

EXAMPLE 26
2-methoxyphenyl-8-quinoyl carbamate

EXAMPLE 27
4-Methoxyphenyl-8-quinolyl Urea

A solution of 8-aminoquinoline (5.2 g.) and 2-methoxyphenylisocyanate (6.8 g.) in ether (200 ml) was stirred at room temperature overnight. The reaction was filtered and dried giving 4.7 g. (42% yield) of solid; m.p. 159°–163° C.

EXAMPLE 28
8-(4-Methoxyphenylcarbamoyl)-quinolin)-5-sulfonic acid, Triethylamine A solution of 8-hydroxyquinolin-5-sulfonic acid (Aldrich H5875-7) triethylamine salt (19 g.) in dimethylformamide (25 ml) was treated with 4-mehtoxyphenyl isocyanate (0.94 g.) and stirred overnight at room temperature. The mixture was triturated with ethyl ether (three times) and a crystalline solid formed which was filtered, washed with ethyl ether and dried (2.3 g.), 92% yield); m.p. 138°–141° C.

EXAMPLE 29
8-Quinolyl-4-methoxy Acetanilide

A mixture of α-chloro-4-methoxy acetanilide (5 g.), 8-quinolinol (3.7 g.), prepared from chloroacetyl chloride (Aldrich 10449-3) and aniline (Aldrich 24228-4), cesium carbonate (24.5 g.), cesium iodide (20 mg.) and acetone (200 ml) was heated to reflux and stirred overnight at room temperature. The reaction was filtered and the solvent was removed in vacuo. The remaining oil was dissolved in methylene chloride, washed with 1N sodium hydroxide, water, dried (MgSO$_4$) and concentrated. The material was crystallized from methylene chloride (2.5 g., 32% yield); m.p. 125°–128° C.

EXAMPLE 30

8-Quinoloyl-4-methoxyphenylAcetate

To a solution of 8-quinolinol (3.9 g.) and triethylamine (2.7 g.) in dry THF (300 ml) was added 4-methoxyphenyl acetyl chloride. The solution was stirred for two days at room temperature. The reaction was filtered and the solvent was removed in vacuo. The remaining solid was recrystallized in ether (3.5 g., 44% yield); m.p. 82°–84° C.

In like manner as above, using appropriate starting materials and reagents, the following compound was made:

EXAMPLE 31

8-quinolyl-4-methoxy benzoate

The compounds of the present invention exhibited activity in the myocardial lipase assay and the rat adipocyte assays.

Myocardial Lipase Assay

All compounds were dissolved in DMSO (final concentration 3.0%) and tested in duplicate at a concentration of 100 μM. Canine cardiac lipases were obtained by extracting washed heart membranes with buffer plus heparine and a small amount of Triton X-100 detergent. Because these enzymes are only active at an oil-water interface, the enzyme reaction is run in an oil-water emulsion that contains triolein substrate, Tris buffer (50mM, pH 6.8) and a small amount of bovine serum albumin (0.5%) added to stabilize the emulsion. A small amount of tritiated triolein was added to the unlabelled triolein substrate. Tritium-labelled oleic acid released by the lipases was extracted into hexane, separated from unreacted triolein and counted in a scintillation counter. Inhibitory agents reduce the amount of radioactivity appearing in the free fatty acid fraction isolated in the extraction procedure.

RAT ADIPOCYTE ASSAY

Abdominal fat pads were removed from male rats weighing 200–250 grams and placed in Krebs-bicarbonate buffer gassed with 95% O$_2$/5% CO$_2$. The fat pads were digested with collagenase for 1 hour at 37° C., washed twice with Krebs-bicarbonate buffer and distributed among a set of 20 ml plastic counting vials. Two such vials received only buffer and cells (4 ml) but no agonists or antagonists. The remaining vials received epinephrine (3 μM) plus the phosphodiesterase inhibitor methylisobutylxanthine (10 μM). Test compounds were dissolved in DMSO or water to a concentration of 20 μM and 40 ml was added to the buffer plus cells in the counting vials. The final compound concentration for routine screening was 200 μM (final concentration of DMSO=1%).

The cells were incubated for 1 hour at 37° C. under a 95% O$_2$/5% CO$_2$ atmosphere. The incubation was stopped by placing the vials in crushed ice. The cells and medium were transferred to test tubes, centrifuged and the cell layer removed by aspiration. The aqueous phase was assayed for glycerol using the enzyme glycerol dehydrogenase.

The glycerol dehydrogenase assay for glycerol depends on the enzyme catalyzed conversion of glycerol to glyceraldehyde and NAD to NADH. The assay can detect as little as 5–10 nanomoles of glycerol. The aqueous phase, following removal of cells, usually contained about 50 to 80 nanomoles of glycerol per 300 μl of assayed sample if no inhibitory activity was present. Samples from the control tubes (no agonist) usually contained 0–5 nanomoles of glycerol per 300 μl of sample.

The results obtained on representative compounds of the present invention are shown in Table I.

TABLE I

INHIBITION OF MYOCARDIAL LIPASE AND RAT ADIPOCYTE LIPOLYSIS BY QUINOLINE CARBANILATES

| No. | X | Y | R$_2$ | R$_1$ | M.P. °C. | Lipase I$_{50}$ μM or % Inh. at 100 μM | Adipocyte I$_{50}$ μM or % Inhib. at μM |
|---|---|---|---|---|---|---|---|
| 1 | 8-O | NH | 4-OCH$_3$ | H | 129–130 | 17 μM | 0.1 μM |
| 2 | 8-O | NH | 2-OCH$_3$ | H | 117–118 | 40 μM | 7 μM |
| 3 | 8-O | NH | 3-OCH$_3$ | H | | 18 μM | 7 μM |
| 4 | 8-NH | O | 4-OCH$_3$ | H | 128–129 | 75% | 3% at 30 μM |
| 5 | 8-NH | O | 2-OCH$_3$ | H | 133–136 | 20 μM | 30 μM |
| 6 | 8-NH | NH | 2-OCH$_3$ | H | 159–163 | 7300 μM | 4% at 200 μM |
| 7 | 8-O | NH | 4-CO$_2$Et | H | 200–203 | 200 μM | 44% at 200 μM |
| 8 | 8-O | NH | 4-Cl | H | 169–171 | 58% | 52% at 3 μM |
| 9 | 8-O | NH | 3-Cl | H | 142–144 | 41% | 5% at 3 μM |
| 10 | 8-O | NH | 2-Cl | H | 116–119 | 1% | — |
| 11 | 8-O | NH | 4=CH$_3$ | H | | 63% | 76% at 3 μM |
| 12 | 8-O | NH | 3-CH$_3$ | H | | 64% | 84% at 3 μM |
| 13 | 8-O | NH | 2-CH$_3$ | H | 130–131 | 7% | 40% at 3 μM |
| 14 | 8-O | NH | 3-CF$_3$ | H | 117–119 | 56% | 7% at 3 μM |
| 15 | 8-O | NH | 2-OCH$_3$ 4-OCH$_3$ | H | 139–141 | 65% | 0.2 μM |
| 16 | 8-O | NH | 2-OCH$_3$ 5-OCH$_3$ | H | | 48 μM | 10 μM |
| 17 | 8-O | NH | 4-Br | H | | 80 μM | 5% at 3 μM |
| 18 | 8-O | NH | H | H | 160–163 | 69% | 28% at 3 μM |
| 19 | 8-O | NH | H | 2-CH$_3$ | 149–151 | 68% | 29% at 3 μM |
| 20 | 8-O | NH | 4-OCH$_3$ | 2-CH$_3$ | 132–134 | 68% | 0.2 μM |

TABLE I-continued
INHIBITION OF MYOCARDIAL LIPASE AND RAT ADIPOCYTE LIPOLYSIS BY QUINOLINE CARBANILATES

| No. | X | Y | $R_2$ | $R_1$ | M.P. °C. | Lipase $I_{50}$ μM or % Inh. at 100 μM | Adipocyte $I_{50}$ μM or % Inhib. at μM |
|---|---|---|---|---|---|---|---|
| 21 | 8-O | NH | 4-Br | 2-$CH_3$ | | 68% | 5% at 3 μM |
| 22 | 8-O | NH | H | 5-Cl | | 69% | 4% at 3 μM |
| 23 | 8-O | NH | 4-$OCH_3$ | 5-$SO_3^-Et_3N^+$ | 138–141 | 83% | 14% at 200 μM |
| 24 | 8-O | NH | H | 5-Cl 7-Cl | | 56% | 28% at 200 μM |
| 25 | 8-$OCH_2$ | NH | 4-$OCH_3$ | H | 125–128 | 7% | 26% at 100 μM |
| 26 | 8-O | H NCH₂ | 4-$OCH_3$ | H | 126–129 | 72% | 5.8 μM |
| 27 | 8-O | H NCH₂CH₂ | 4-$OCH_3$ | H | 165–167 | 70% | 98% at 100 μM |
| 28 | 8-O | HCH₃ NCH(S) | H | H | 126–128 | 76% | 35 μM |
| 29 | 8-O | HCH₃ NCH(R) | H | H | 126–128 | 74% | 35 μM |
| 30 | 8-O | $CH_2$ | 4-$OCH_3$ | H | 82–84 | 0% | 74% at 100 μM |
| 31 | 8-O | — | 4-$OCH_3$ | H | 164–167 | 13% | 49% at 200 μM |

The therapeutic compounds of this invention may be administered to a mammal alone or in combination with pharmaceutically acceptable carriers, the proportion of which is determined by the solubility and chemical nature of the compound, chosen route of administration and standard pharmaceutical practice.

The physician will determine the dosage of the present therapeutic agents which will be most suitable and it will vary with the form of administration and the particular compound chosen, and also, it will vary with the particular patient under treatment. He will generally wish to initiate treatment with small dosages substantially less than the optimum dose of the compound and increase the dosage by small increments until the optimum effect under the circumstances is reached. The therapeutic dosage will generally be from a couple of mg. to about 30 mg/kg of body weight or higher.

What is claimed is:
1. A therapeutic composition for the inhibition of lipolysis in mammals which comprises, as an active ingredient, an effective amount to effect inhibition of lipolysis in said mammals of a member of the formula

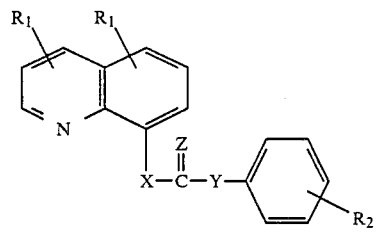

and pharmaceutically acceptable salts thereof wherein:
$R_1$ is H, alkyl, alkoxy, trihalomethyl, chlorine;
X is in the 8 position and is $O(CH_2)_n$, or $N(CH_2)_n$;
Y is $O(CH_2)_n$, $N(CH_2)_n$;
$R_2$ is monosubstituted or independently disubstituted H, carboxyl or alkylcarboxy;
Z is O; and
n is 0 to 10 inclusive, wherein the alkyl group and the alkyl moieties in alkoxy and alkylcarboxy having from 1 to 7 carbon atoms, in a pharmaceutically acceptable carrier.

2. A pharmaceutical composition for the inhibition of lipolysis in mammals which comprises, as an active ingredient, an effective amount of 8-quinolyl-carbanilate in a pharmaceutically acceptable carrier.

3. A pharmaceutical composition for the inhibition of lipolysis in mammals which comprises, as an active ingredient, an effective amount of 2-methyl-8-quinolyl carbanilate in a pharmaceutically acceptable carrier.

* * * * *